US006150774A

United States Patent [19]
Mueller et al.

[11] Patent Number: 6,150,774
[45] Date of Patent: *Nov. 21, 2000

[54] MULTICOLORED LED LIGHTING METHOD AND APPARATUS

[75] Inventors: George G. Mueller, Boston, Mass.; Ihor Lys, Pittsburgh, Pa.

[73] Assignee: Color Kinetics, Incorporated, Boston, Mass.

[*] Notice: This patent is subject to a terminal disclaimer.

[21] Appl. No.: 09/425,770

[22] Filed: Oct. 22, 1999

Related U.S. Application Data

[63] Continuation of application No. 08/920,156, Aug. 26, 1997, Pat. No. 6,016,038.

[51] Int. Cl.[7] .................................................. H05B 37/02
[52] U.S. Cl. ........................... 315/291; 315/292; 315/312; 315/362
[58] Field of Search .................................... 315/291, 292, 315/295, 300, 308, 312, 302, 314, 76, 360, 362

[56] References Cited

U.S. PATENT DOCUMENTS

| | | | |
|---|---|---|---|
| 3,746,918 | 7/1973 | Drucker et al. | 315/77 |
| 4,298,869 | 11/1981 | Okuno | 340/782 |
| 4,329,625 | 5/1982 | Nishizawa et al. | 315/158 |
| 4,367,464 | 1/1983 | Kurahashi et al. | 340/701 |
| 4,388,567 | 6/1983 | Yamazaki et al. | 315/291 |
| 4,420,711 | 12/1983 | Takahashi et al. | 315/296 |
| 4,625,152 | 11/1986 | Nakai | 315/317 |
| 4,727,289 | 2/1988 | Uchika | 315/71 |
| 4,740,882 | 4/1988 | Miller | 364/132 |
| 4,845,481 | 7/1989 | Havel | 340/762 |
| 4,887,074 | 12/1989 | Simon et al. | 340/782 |
| 4,992,704 | 2/1991 | Stinson | 315/167 |
| 5,003,227 | 3/1991 | Nilssen | 315/161 |
| 5,008,595 | 4/1991 | Kazar | 315/178 |
| 5,126,634 | 6/1992 | Johnson | 315/71 |
| 5,134,387 | 7/1992 | Smith et al. | 340/701 |
| 5,164,715 | 11/1992 | Kashiwabara et al. | 340/716 |
| 5,184,114 | 2/1993 | Brown | 340/701 |
| 5,226,723 | 7/1993 | Chen | 362/241 |
| 5,254,910 | 10/1993 | Yang | 315/313 |
| 5,256,948 | 10/1993 | Boldin et al. | 315/313 |
| 5,282,121 | 1/1994 | Bornhorst et al. | 362/294 |
| 5,294,865 | 3/1994 | Haraden | 315/58 |

(List continued on next page.)

FOREIGN PATENT DOCUMENTS

| | | |
|---|---|---|
| 0752 632 A2 | 1/1997 | European Pat. Off. . |
| 2 640 791 | 6/1990 | France . |
| 060 43830 | 2/1994 | Japan . |
| 2 176 042 | 12/1986 | United Kingdom . |

OTHER PUBLICATIONS

Bhatnagar et al., "Exploration of Antileishmanial Activity in Heterocycles; Result of their in vivo & in vitro bioevaluations", Indian Journal of Medical Research89: 439–444 (Nov. 1989).

Berman D. J., "Human Leishmaniasis: Clinical, Diagnostic, and Chemotherapeutic Developments in the Last 10 Years", Clinical Infectious Diseases 24:684–703 (1997).

Bhafnagar et al., "Exploration of Antileishmanial Activity in Heterocycles; Result of their in vivo & in vitro bioevaluations", Indian Journal of Medical Research89: 439–444 (Nov. 1989).

(List continued on next page.)

*Primary Examiner*—Haissa Philogene
*Attorney, Agent, or Firm*—Foley, Hoag, & Eliot LLP

[57] ABSTRACT

The systems and methods described herein relate to LED systems capable of generating light, such as for illumination or display purposes. The light-emitting LEDs may be controlled by a processor to alter the brightness and/or color of the generated light, e.g., by using pulse-width modulated signals. Thus, the resulting illumination may be controlled by a computer program to provide complex, predesigned patterns of light in virtually any environment.

11 Claims, 6 Drawing Sheets

U.S. PATENT DOCUMENTS

| | | | |
|---|---|---|---|
| 5,350,977 | 9/1994 | Hamamoto et al. | 315/291 |
| 5,357,170 | 10/1994 | Luchaco et al. | 315/159 |
| 5,374,876 | 12/1994 | Horibata et al. | 315/313 |
| 5,388,357 | 2/1995 | Malita | 40/570 |
| 5,404,282 | 4/1995 | Klinke et al. | 362/249 |
| 5,410,328 | 4/1995 | Yoksza et al. | 345/82 |
| 5,420,482 | 5/1995 | Phares | 315/292 |
| 5,436,535 | 7/1995 | Yang | 315/313 |
| 5,463,280 | 10/1995 | Johnson | 315/187 |
| 5,504,395 | 4/1996 | Johnson et al. | 315/71 |
| 5,545,950 | 8/1996 | Cho | 315/56 |
| 5,561,346 | 10/1996 | Byrne | 313/512 |
| 5,575,459 | 11/1996 | Anderson | 362/240 |
| 5,592,051 | 1/1997 | Korkala | 315/210 |
| 5,751,118 | 5/1998 | Mortimer | 315/291 |
| 5,821,685 | 10/1998 | Vilanilam et al. | 315/58 |
| 6,016,038 | 1/2000 | Mueller et al. | 315/291 |

OTHER PUBLICATIONS

El Roufaie Mohammed et al., "ELISA Using Intact Promastigotes for Immunodiagnosis of Kala–azar", Transactions of the Royal Society of Tropical Medicine and Hygiene, 79(3): 344–350 (1985).

Gupta et al., A Rising Trend in Kala–azar in Varanasi District, Uttar Pradesh, India: A Recent Survey Using Direct Agglutination Test', Current Science 73(5):456–459 (1997).

Harith et al., "Application of a Direct Agglutination Test for Detection Specific Anti–Leishmania Antibodies in the Canine Reservoir", Journal of Clinical Microbiology, 27(10):2252–2257 (1989).

Harith et al., "A Simple and Economical Direct Agglutination Test for Serodiagnosis and Sero–epidemiological studies of Visceral Leishmaniasis", Transactions of the Royal Society of Tropical Medicine and Hygiene, 80:583–587(1986).

Harith et al., "Improvement of a Direct Agglutination Test for field Studies of Visceral Leishmaniasis", Journal of Clinical Microbiology, 26(7):1321–1325 (1988).

Jaffe and McMahon–Pratt., "Serodiagnostic Assay for Visceral Leishmaniasis Employing Monoclonal Antibodies", Transactions of the Royal Society of Tropical Medicine and Hygiene, 81:587–594 (1987).

Jahn and Diesfeld; "Evaluation of a Visually Read ELISA for Serodiagnosis and Sero–epidemiological Studies of Kala–azar in the Baringo District, Kenya", Transactions of the Royal Society of Tropical Medicine and Hygiene, 77(4): 451–454 (1983).

Kohanteb et al., "Detection of Leishmania Donovani Soluble Antigen and Antibody in the Urine of Visceral Leishmaniasis Patients", Transactions of the Royal Society of Tropical Medicine and Hygiene, 81:578–580 (1987).

Manning et al., "Approaches for Increasing the Solution Stability of Proteins", Biotechnology and Bioingineering, 48: 506–512 (1995).

Mengistu et al., "The Value of a Direct Agglutination test in the Diagnosis of Cutaneous and Visceral Leishmaniasis in Ethiopia", Transactions of the Royal Society of Tropical Medicine and Hygiene, 84:359–362 (1990).

Naik et al., "Kala–azar in North–western India: A Studie of 24 Patients", Transactions of the Royal Society of Tropical Medicine and Hygiene73(1):61–65 (1979).

MULTICOLORED LED LIGHTING METHOD AND APPARATUS

This application is a continuation of Ser. No. 08/920,156, filed on Aug. 26, 1997, now U.S. Pat. No. 6,016,038, entitled Multicolored Led Lighting Method and Apparatus.

BACKGROUND OF THE INVENTION

The present invention relates to providing light of a selectable color using LEDs. More particularly, the present invention is a method and apparatus for providing multicolored illumination. More particularly still, the present invention is an apparatus for providing a computer controlled multicolored illumination network capable of high performance and rapid color selection and change.

It is well known that combining the projected light of one color with the projected light of another color will result in the creation of a third color. It is also well known that the three most commonly used primary colors—red, blue and green—can be combined in different proportions to generate almost any color in the visible spectrum. The present invention takes advantage of these effects by combining the projected light from at least two light emitting diodes (LEDs) of different primary colors.

Computer lighting networks are not new. U.S. Pat. No. 5,420,482, issued to Phares. describes one such network that uses different colored LEDs to generate a selectable color. Phares is primarily for use as a display apparatus. However, the apparatus has several disadvantages and limitations. First, each of the three color LEDs in Phares is powered through a transistor biasing scheme in which the transistor base is coupled to a respective latch register through biasing resistors. The three latches are all simultaneously connected to the same data lines on the data bus. This means it is impossible in Phares to change all three LED transistor biases independently and simultaneously. Also, biasing of the transistors is inefficient because power delivered to the LEDs is smaller than that dissipated in the biasing network. This makes the device poorly suited for efficient illumination applications. The transistor biasing used by Phares also makes it difficult, if not impossible, to interchange groups of LEDs having different power ratings, and hence different intensity levels.

U.S. Pat. No. 4,845,481, issued to Havel, is directed to a multicolored display device. Havel addresses some, but not all of the switching problems associated with Phares. Havel uses a pulse width modulated signal to provide current to respective LEDs at a particular duty cycle. However, no provision is made for precise and rapid control over the colors emitted. As a stand alone unit, the apparatus in Havel suggests away from network lighting, and therefore lacks any teaching as to how to implement a pulse width modulated computer lighting network. Further, Havel does not appreciate the use of LEDs beyond mere displays, such as for illumination.

U.S. Pat. No. 5,184,114, issued to Brown, shows an LED display system. But Brown lacks any suggestion to use LEDs for illumination, or to use LEDs in a configurable computer network environment. U.S. Pat. No. 5,134,387, issued to Smith et al., directed to an LED matrix display, contains similar problems. Its rudimentary current control scheme severely limits the possible range of colors that can be displayed.

It is an object of the present invention to overcome the limitations of the prior art by providing a high performance computer controlled multicolored LED lighting network.

It is a further object of the present invention to provide a unique LED lighting network structure capable of both a linear chain of nodes and a binary tree configuration.

It is still another object of the present invention to provide a unique heat-dissipating housing to contain the lighting units of the lighting network.

It is yet another object of the present invention to provide a current regulated LED lighting apparatus, wherein the apparatus contains lighting modules each having its own maximum current rating and each conveniently interchangeable with one another.

It is a still further object of the present invention to provide a unique computer current controlled LED lighting assembly for use as a general illumination device capable of emitting multiple colors in a continuously programmable 24-bit spectrum.

It is yet a still further object of the present invention to provide a unique flashlight, inclinometer, thermometer, general environmental indicator and lightbulb, all utilizing the general computer current-control principles of the present invention.

Other objects of the present invention will be apparent from the detailed description below.

SUMMARY OF THE INVENTION

In brief, the invention herein comprises a pulse width modulated current control for an LED lighting assembly, where each current-controlled unit is uniquely addressable and capable of receiving illumination color information on a computer lighting network. In a further embodiment, the invention includes a binary tree network configuration of lighting units (nodes). In another embodiment, the present invention comprises a heat dissipating housing, made out of a heat-conductive material, for housing the lighting assembly. The heat dissipating housing contains two stacked circuit boards holding respectively the power module and the light module. The light module is adapted to be conveniently interchanged with other light modules having programmable current. and hence maximum light intensity, ratings. Other embodiments of the present invention involve novel applications for the general principles described herein.

DETAILED DESCRIPTION

Figure 1:
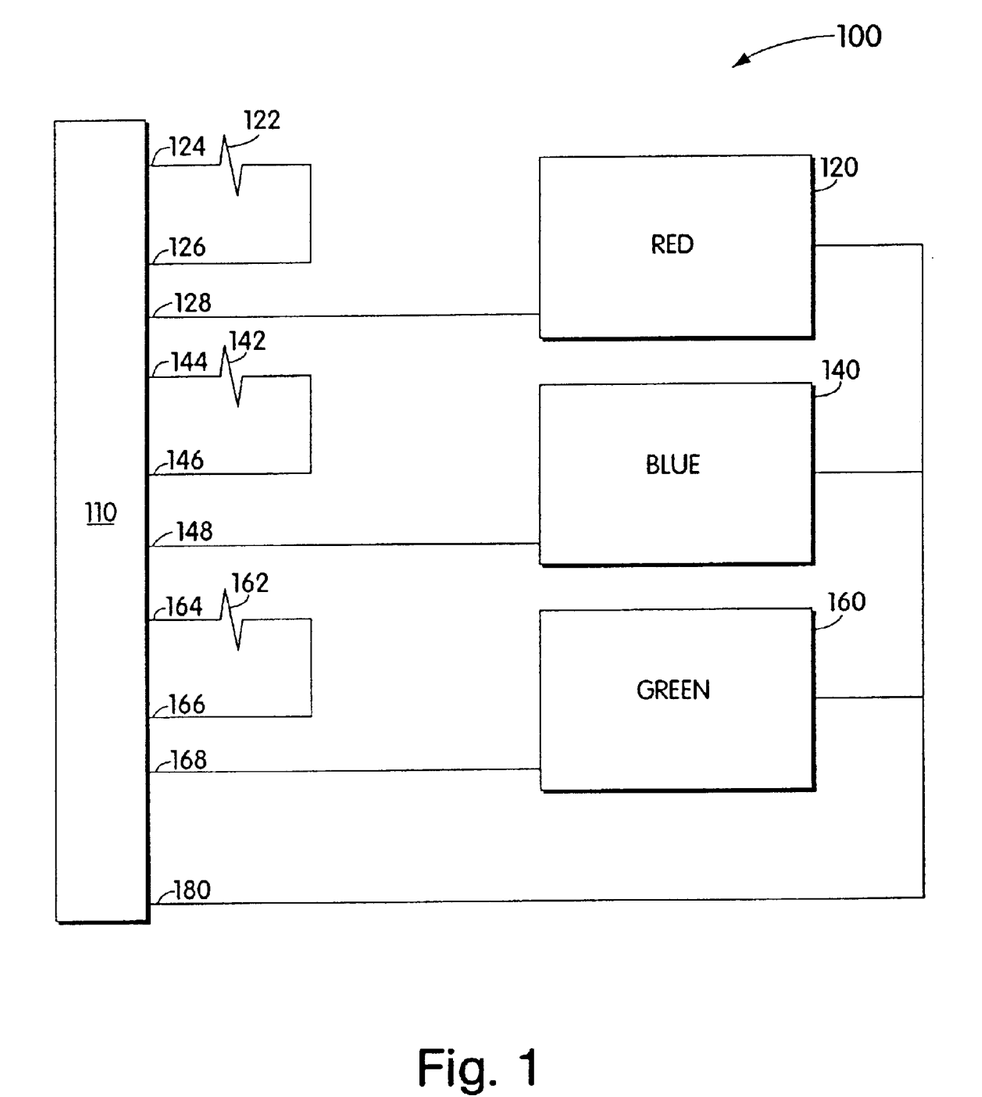
FIG. 1 is a stylized electrical circuit schematic of the light module of the present invention.
Figure 4:
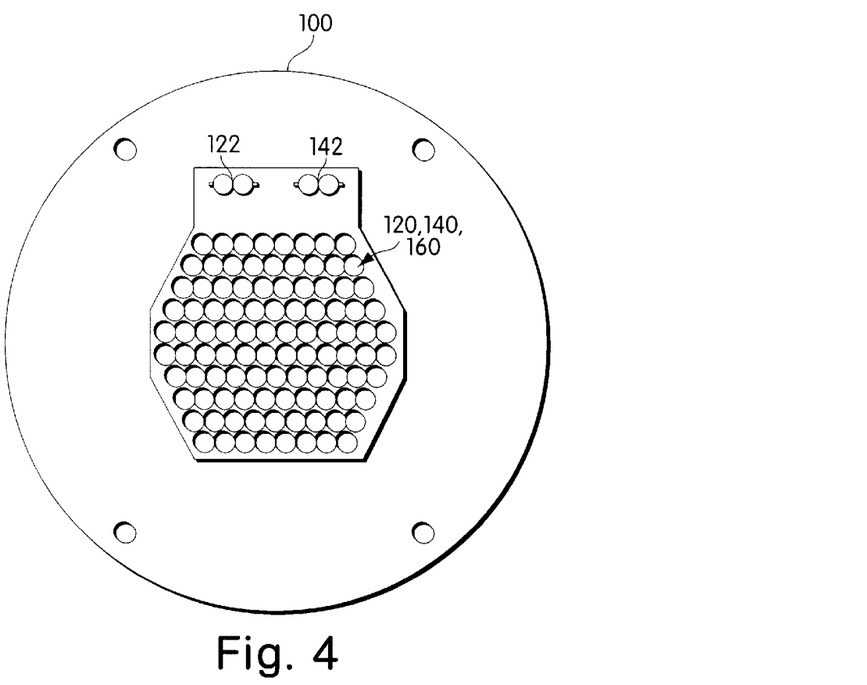
FIG. 4 is a plan view of the LED-containing side of the light module of the present invention.
Figure 5:
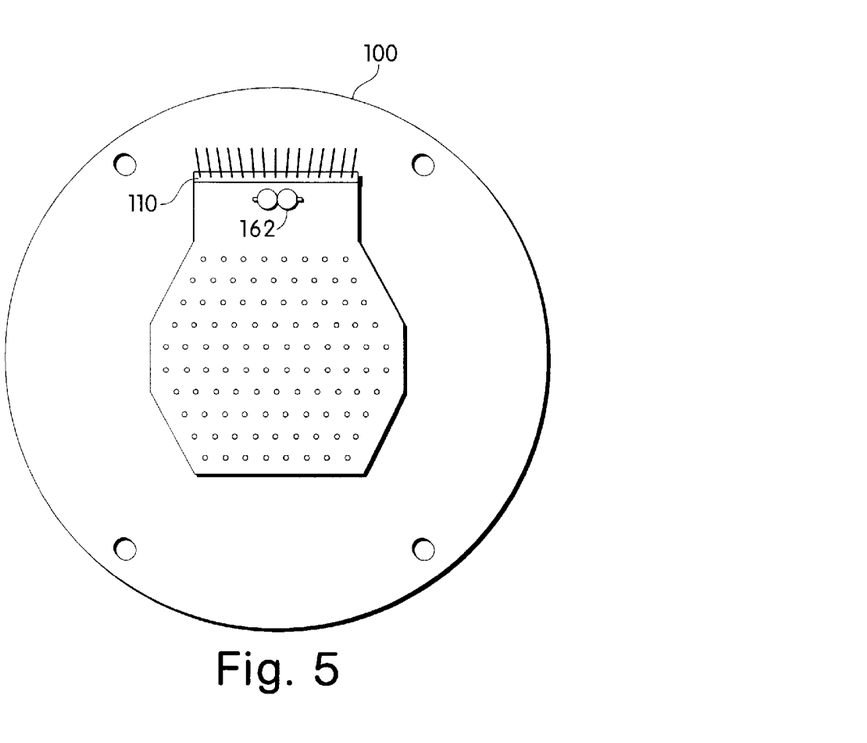
FIG. 5 is a plan view of the electrical connector side of the light module of the present invention.

The structure and operation of a preferred embodiment will now be described. It should be understood that many other ways of practicing the inventions herein are available, and the embodiments described herein are exemplary and not limiting. Turning to FIG. 1, shown is an electrical schematic representation of a light module 100 of the present invention. FIGS. 4 and 5 show the LED-containing side and the electrical connector side of light module 100. Light module 100 is self-contained, and is configured to be a standard item interchangeable with any similarly constructed light module. Light module 100 contains a ten-pin electrical connector 110 of the general type. In this embodiment, the connector 110 contains male pins adapted to fit into a complementary ten-pin connector female assembly, to be described below. Pin 180 is the power supply. A source of DC electrical potential enters module 100 on pin 180. Pin 180 is electrically connected to the anode end of light emitting diode (LED) sets 120, 140 and 160 to establish a uniform high potential on each anode end.

LED set 120 contains red LEDs, set 140 contains blue and set 160 contains green, each obtainable from the Nichia America Corporation. These LEDs are primary colors, in the sense that such colors when combined in preselected proportions can generate any color in the spectrum. While three primary colors is preferred, it will be understood that the present invention will function nearly as well with only two primary colors to generate any color in the spectrum. Likewise, while the different primary colors are arranged herein on sets of uniformly colored LEDs, it will be appreciated that the same effect may be achieved with single LEDs containing multiple color-emitting semiconductor dies. LED sets 120, 140 and 160 each preferably contains a serial/parallel array of LEDs in the manner described by Okuno in U.S. Pat. No. 4,298,869, incorporated herein by reference. In the present embodiment, LED set 120 contains three parallel connected rows of nine red LEDs (not shown), and LED sets 140 and 160 each contain five parallel connected rows of five blue and green LEDs, respectively (not shown). It is understood by those in the art that, in general, each red LED drops the potential in the line by a lower amount than each blue or green LED, about 2.1 V, compared to 4.0 V, respectively, which accounts for the different row lengths. This is because the number of LEDs in each row is determined by the amount of voltage drop desired between the anode end at the power supply voltage and the cathode end of the last LED in the row. Also, the parallel arrangement of rows is a fail-safe measure that ensures that the light module 100 will still function even if a single LED in a row fails, thus opening the electrical circuit in that row. The cathode ends of the three parallel rows of nine red LEDs in LED set 120 are then connected in common, and go to pin 128 on connector 110. Likewise, the cathode ends of the five parallel rows of five blue LEDs in LED set 140 are connected in common, and go to pin 148 on connector 110. The cathode ends of the five parallel rows of five green LEDs in LED set 160 are connected in common, and go to pin 168 on connector 110. Finally, on light module 100, each LED set is associated with a programming resistor that combines with other components, described below, to program the maximum current through each set of LEDs. Between pin 124 and 126 is resistor 122, 6.2 Ω. Between pin 144 and 146 is resistor 142. 4.7 Ω. Between pin 164 and 166 is resistor 162, 4.7 Ω. Resistor 122 programs maximum current through red LED set 120. resistor 142 programs maximum current through blue LED set 140, and resistor 162 programs maximum current through green LED set 160. The values these resistors should take are determined empirically, based on the desired maximum light intensity of each LED set. In the present embodiment, the resistances above program red, blue and green currents of 70, 50 and 50 µA, respectively.

Figure 2:
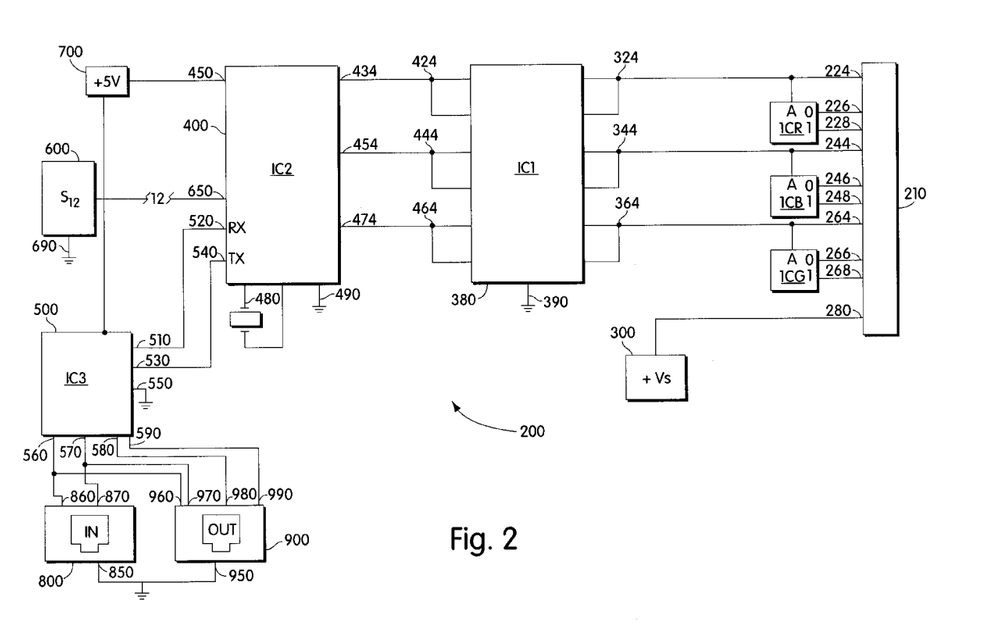
FIG. 2 is a stylized electrical circuit schematic of the power module of the present invention.
Figure 6:
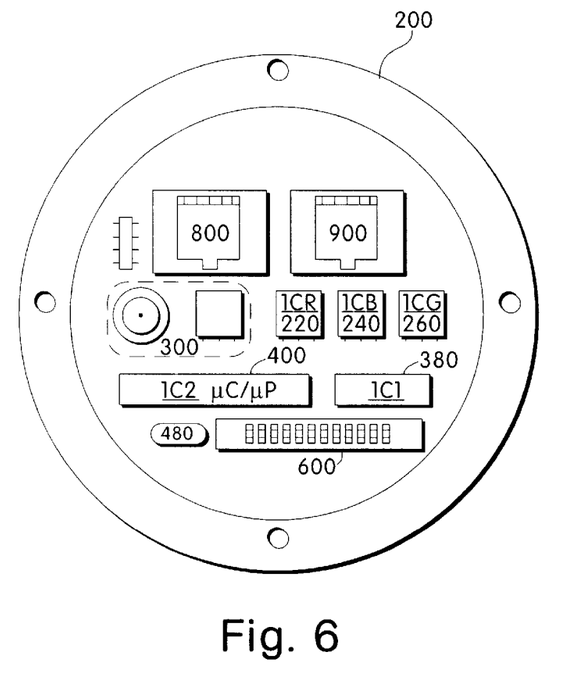
FIG. 6 is a plan view of the power terminal side of the power module of the present invention.
Figure 7:
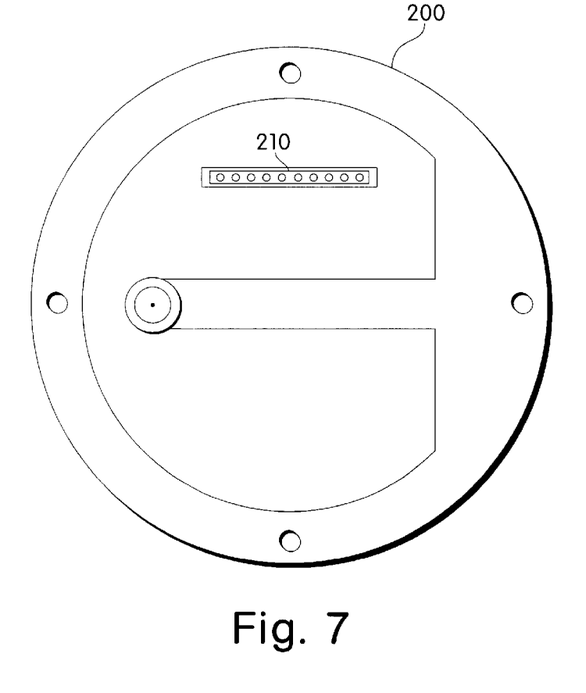
FIG. 7 is a plan view of the electrical connector side of the power module of the present invention.

With the electrical structure of light module 100 described, attention will now be given to the electrical structure of power module 200, shown in FIG. 2. FIGS. 6 and 7 show the power terminal side and electrical connector side of an embodiment of power module 200. Like light module 100, power module 200 is self contained. Interconnection with male pin set 110 is achieved through complementary female pin set 210. Pin 280 connects with pin 180 for supplying power, delivered to pin 280 from supply 300. Supply 300 is shown as a functional block for simplicity. In actuality, supply 300 can take numerous forms for generating a DC voltage. In the present embodiment, supply 300 provides 24 Volts through a connection terminal (not shown), coupled to pin 280 through transient protection capacitors (not shown) of the general type. It will be appreciated that supply 300 may also supply a DC voltage after rectification and/or voltage transformation of an AC supply, as described more fully in U.S. Pat. No. 4,298,869.

Also connected to pin connector 210 are three current programming integrated circuits, ICR 220, ICB 240 and ICG 260. Each of these is a three terminal adjustable regulator, preferably part number LM317B, available from the National Semiconductor Corporation, Santa Clara. Calif. The teachings of the LM317 datasheet are incorporated herein by reference. Each regulator contains an input terminal, an output terminal and an adjustment terminal, labeled I. O and A. respectively. The regulators function to maintain a constant maximum current into the input terminal and out of the output terminal. This maximum current is pre-programmed by setting a resistance between the output and the adjustment terminals. This is because the regulator will cause the voltage at the input terminal to settle to whatever value is needed to cause 1.25 V to appear across the fixed current set resistor, thus causing constant current to flow. Since each functions identically, only ICR 220 will now be described. First, current enters the input terminal of ICR 220 from pin 228. Of course, pin 228 in the power module is coupled to pin 128 in the light module, and receives current directly from the cathode end of the red LED set 120. Since resistor 122 is ordinarily disposed between the output and adjustment terminals of ICR 220 through pins 224/124 and 226/126, resistor 122 programs the amount of current regulated by ICR 220. Eventually, the current output from the adjustment terminal of ICR 220 enters a Darlington driver. In this way, ICR 220 and associated resistor 122 program the maximum current through red LED set 120. Similar results are achieved with ICB 240 and resistor 142 for blue LED set 140, and with ICG 260 and resistor 162 for green LED set 160.

The red, blue and green LED currents enter another integrated circuit, IC1 380, at respective nodes 324, 344 and 364. IC1 380 is preferably a high current/voltage Darlington driver, part no. DS2003 available from the National Semiconductor Corporation, Santa Clara, Calif. IC1 380 is used as a current sink, and functions to switch current between respective LED sets and ground 390. As described in the DS2003 datasheet, incorporated herein by reference. IC1 contains six sets of Darlington transistors with appropriate on-board biasing resistors. As shown, nodes 34, 344 and 364 couple the current from the respective LED sets to three pairs of these Darlington transistors. in the well known manner to take advantage of the fact that the current rating of IC1 330 may be doubled by using pairs of Darlington transistors to sink respective currents. Each of the three on-board Darlington pairs is used in the following manner as a switch. The base of each Darlington pair is coupled to signal inputs 424, 444 and 464, respectively. Hence, input 424 is the signal input for switching current through node 324, and thus the red LED set 120. Input 444 is the signal input for switching current though node 344, and thus the blue LED set 140. Input 464 is the signal input for switching current through node 364, and thus the green LED set 160. Signal inputs 424, 444 and 464 are coupled to respective signal outputs 434, 454 and 474 on microcontroller IC2 400, as described below. In essence, when a high frequency square wave is incident on a respective signal input, IC1 330 switches current through a respective node with the identical frequency and duty cycle. Thus, in operation, the states of signal inputs 424, 444 and 464 directly correlate with the opening and closing of the power circuit through respective LED sets 120, 140 and 160.

The structure and operation of microcontroller IC2 400 will now be described. Microcontroller IC2 400 is preferably a MICROCHIP brand PIC16C63, although almost any properly programmed microcontroller or microprocessor can perform the software functions described herein. The main function of microcontroller IC2 400 is to convert numerical data received on serial Rx pin 520 into three independent high frequency square waves of uniform frequency but independent duty cycles on signal output pins 434, 454 and 474. The FIG. 2 representation of microcontroller IC2 400 is partially stylized, in that persons of skill in the art will appreciate that certain of the twenty-eight standard pins have been omitted or combined for greatest clarity.

Microcontroller IC2 400 is powered through pin 450, which is coupled to a 5 Volt source of DC power 700. Source 700 is preferably driven from supply 300 through a coupling (not shown) that includes a voltage regulator (not shown). An exemplary voltage regulator is the LM340 3-terminal positive regulator, available from the National Semiconductor Corporation, Santa Clara, Calif. The teachings of the LM340 datasheet are hereby incorporated by reference. Those of skill in the art will appreciate that most microcontrollers, and many other independently powered digital integrated circuits, are rated for no more than a 5 Volt power source. The clock frequency of microcontroller IC2 400 is set by crystal 480, coupled through appropriate pins. Pin 490 is the microcontroller IC2 400 ground reference.

Switch 600 is a twelve position dip switch that may be alterably and mechanically set to uniquely identify the microcontroller IC2 400. When individual ones of the twelve mechanical switches within dip switch 600 are closed, a path is generated from corresponding pins 650 on microcontroller IC2 400 to ground 690. Twelve switches create $2^{12}$ possible settings, allowing any microcontroller IC2 400 to take on one of 4096 different IDs, or addresses. In the preferred embodiment, only nine switches are actually used because the DMX-512 protocol, discussed below, is employed.

Once switch 600 is set, microcontroller IC2 400 "knows" its unique address ("who am I"), and "listens" on serial line 520 for a data stream specifically addressed to it. A high speed network protocol. preferably a DMX protocol, is used to address network data to each individually addressed microcontroller IC2 400 from a central network controller (not shown). The DMX protocol is described in a United States Theatre Technology. Inc. publication entitled "DMX512/1990 Digital Data Transmission Standard for Dimmers and Controllers," incorporated herein by reference. Basically, in the network protocol used herein, a central controller (not shown) creates a stream of network data consisting of sequential data packets. Each packet first contains a header, which is checked for conformance to the standard and discarded, followed by a stream of sequential bytes representing data for sequentially addressed devices. For instance, if the data packet is intended for light number fifteen, then fourteen bytes from the data stream will be discarded, and the device will save byte number fifteen. If as in the preferred embodiment, more than one byte is needed, then the address is considered to be a starting address, and more than one byte is saved and utilized. Each byte corresponds to a decimal number 0 to 255, linearly representing the desired intensity from Off to Full. (For simplicity, details of the data packets such as headers and stop bits are omitted from this description, and will be well appreciated by those of skill in the art.) This way, each of the three LED colors is assigned a discrete intensity value between 0 and 255. These respective intensity values are stored in respective registers within the memory of microcontroller IC2 400 (not shown). Once the central controller exhausts all data packets, it starts over in a continuous refresh cycle. The refresh cycle is define by the standard to be a minimum of 1196 microseconds, and a maximum of 1 second.

Microcontroller IC2 400 is programmed continually to "listen" for its data stream. When microcontroller IC2 400 is "listening" but before it detects a data packet intended for it. it is running a routine designed to create the square wave signal outputs on pins 434, 454 and 474 The values in the color registers determine the duty cycle of the square wave. Since each register can take on a value from 0 to 255, these values create 256 possible different duty cycles in a linear range from 0% to 100%. Since the square wave frequency is uniform and determined by the program running in the microcontroller IC2 400, these different discrete duty cycles represent variations in the width of the square wave pulses. This is known as pulse width modulation (PWM).

The PWM interrupt routine is implemented using a simple counter, incrementing from 0 to 255 in a cycle during each period of the square wave output on pins 434, 454 and 474. When the counter rolls over to zero, all three signals are set high. Once the counter equals the register value, signal output is changed to low. When microcontroller IC2 400 receives new data, it freezes the counter, copies the new data to the working registers, compares the new register values with the current count and updates the output pins accordingly, and then restarts the counter exactly where it left off. Thus, intensity values may be updated in the middle of the PWM cycle. Freezing the counter and simultaneously updating the signal outputs has at least two advantages. First, it allows each lighting unit to quickly pulse/strobe as a strobe light does. Such strobing happens when the central controller sends network data having high intensity values alternately with network data having zero intensity values at a rapid rate. If one restarted the counter without first updating the signal outputs, then the human eye would be able to perceive the staggered deactivation of each individual color LED that is set at a different pulse width. This feature is not of concern in incandescent lights because of the integrating effect associated with the heating and cooling cycle of the illumination element. LEDs. unlike incandescent elements, activate and deactivate essentially instantaneously in the present application. The second advantage is that one can "dim" the LEDs without the flickering that would otherwise occur if the counter were reset to zero. The central controller can send a continuous dimming signal when it creates a sequence of intensity values representing a uniform and proportional decrease in light intensity for each color LED. If one did not update the output signals before restarting the counter, there is a possibility that a single color LED will go through nearly two cycles without experiencing the zero current state of its duty cycle. For instance, assume the red register is set at 4 and the counter is set at 3 when it is frozen. Here, the counter is frozen just before the "off" part of the PWM cycle is to occur for the red LEDs. Now assume that the network data changes the value in the red register from 4 to 2 and the counter is restarted without deactivating the output signal. Even though the counter is greater than the intensity value in the red register, the output state is still "on", meaning that maximum current is still flowing through the red LEDs. Meanwhile, the blue and green LEDs will probably turn off at their appropriate times in the PWM cycle. This would be perceived by the human eye as a red flicker in the course of dimming the color intensities. Freezing the counter and updating the output for the rest of the PWM cycle overcomes these disadvantages, ensuring the flicker does not occur.

The network interface for microcontroller IC2 400 will now be described. Jacks 800 and 900 are standard RJ-8 network jacks. Jack 800 is used as an input jack, and is shown for simplicity as having only three inputs: signal inputs 860, 870 and ground 850. Network data enters jack 800 and passes through signal inputs 860 and 870. These signal inputs are then coupled to IC3 500, which is an RS-485/RS-422 differential bus repeater of the standard type, preferably a DS96177 from the National Semiconductor Corporation, Santa Clara, Calif. The teachings of the DS96177 datasheet are hereby incorporated by reference. The signal inputs 860, 870 enter IC3 500 at pins 560, 570. The data signal is passed through from pin 510 to pin 520 on microcontroller IC2 400. The same data signal is then returned from pin 540 on IC2 400 to pin 530 on IC3 500. Jack 900 is used as an output jack and is shown for simplicity as having only five outputs: signal outputs 960, 970, 980, 990 and ground 950. Outputs 960 and 970 are split directly from input lines 860 and 870, respectively. Outputs 980 and 990 come directly from IC3 500 pins 580 and 590, respectively. It will be appreciated that the foregoing assembly enables two network nodes to be connected for receiving the network data. Thus, a network may be constructed as a daisy chain, if only single nodes are strung together, or as a binary tree, if two nodes are attached to the output of each single node.

From the foregoing description, one can see that an addressable network of LED illumination or display units can be constructed from a collection of power modules each connected to a respective light module. As long as at least two primary color LEDs are used, any illumination or display color may be generated simply by preselecting the light intensity that each color emits. Further, each color LED can emit light at any of 255 different intensities, depending on the duty cycle of PWM square wave, with a full intensity pulse generated by passing maximum current through the LED. Further still, the maximum intensity can be conveniently programmed simply by adjusting the ceiling for the maximum allowable current using programming resistances for the current regulators residing on the light module. Light modules of different maximum current ratings may thereby be conveniently interchanged.

Figure 3:
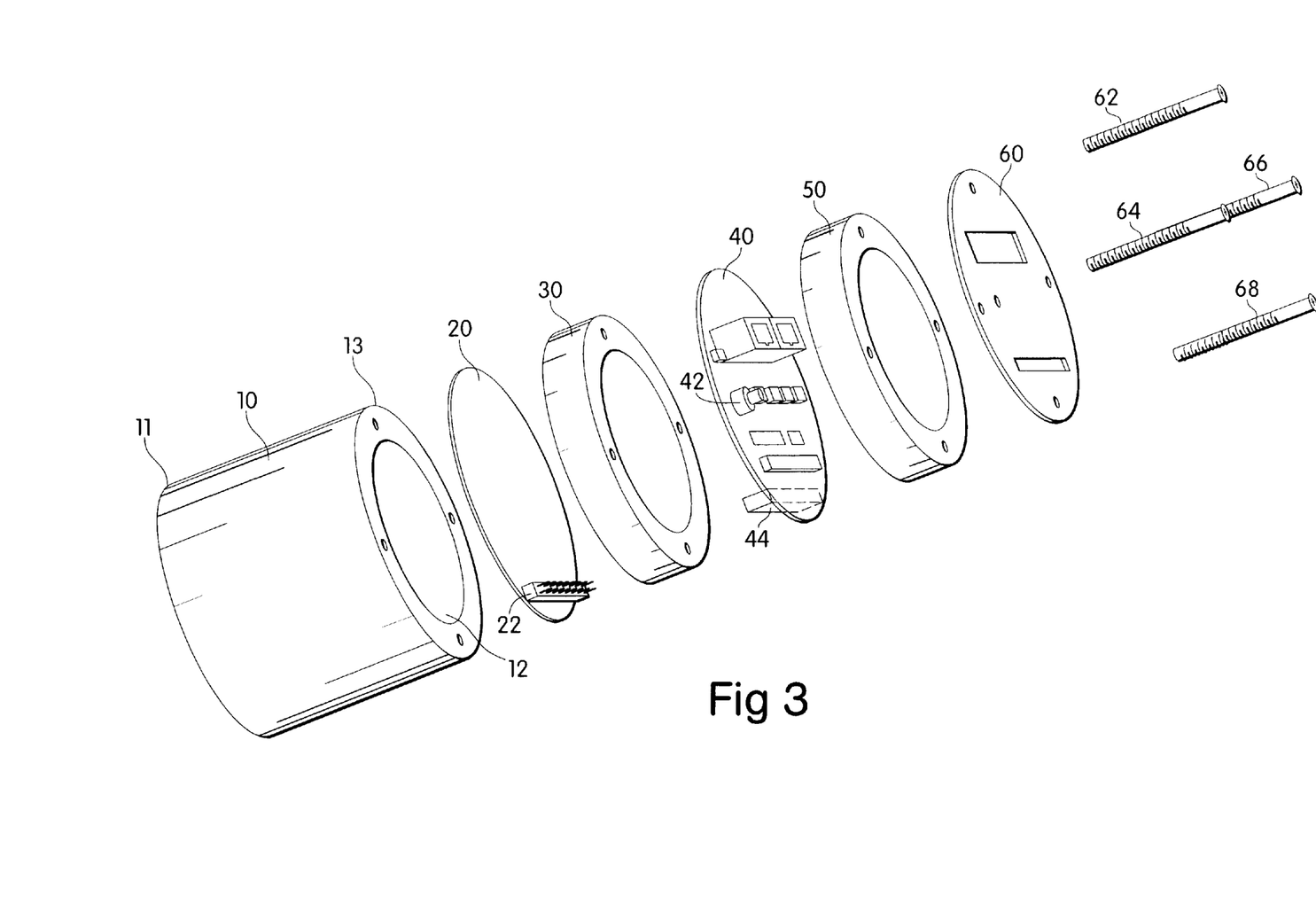
FIG. 3 is an exploded view of the housing of one of the embodiments of the present invention.

The foregoing embodiment may reside in any number of different housings. A preferred housing for an illumination unit is described. Turning now to FIG. 3, there is shown an exploded view of an illumination unit of the present invention comprising a substantially cylindrical body section 10, a light module 20, a conductive sleeve 30, a power module 40, a second conductive sleeve 50, and an enclosure plate 60. It is to be assumed here that the light module 20 and the power module 40 contain the electrical structure and software of light module 100 and power module 200, described above. Screws 62, 64, 66, 68 allow the entire apparatus to be mechanically connected. Body section 10, conductive sleeves 30 and 50 and enclosure plate 60 are preferably made from a material that conducts heat, most preferably aluminum. Body section 10 has an open end 11, a reflective interior portion 12 and an illumination end 13, to which module 20 is mechanically affixed. Light module 20 is disk shaped and has two sides. The illumination side (not shown) comprises a plurality of LEDs of different primary colors. The connection side holds an electrical connector male pin assembly 22. Both the illumination side and the connection side are coated with aluminum surfaces to better allow the conduction of heat outward from the plurality of LEDs to the body section 10. Likewise, power module 40 is disk shaped and has every available surface covered with aluminum for the same reason. Power module 40 has a connection side holding an electrical connector female pin assembly 44 adapted to fit the pins from assembly 22. Power module 40 has a power terminal side holding a terminal 42 for connection to a source of DC power. Any standard AC or DC jack may be used, as appropriate.

Interposed between light module 20 and power module 40 is a conductive aluminum sleeve 30, which substantially encloses the space between modules 20 and 40. As shown, a disk-shaped enclosure plate 60 and screws 62, 64, 66 and 68 seal all of the components together, and conductive sleeve 50 is thus interposed between enclosure plate 60 and power module 40. Once sealed together as a unit, the illumination apparatus may be connected to a data network as described above and mounted in any convenient manner to illuminate an area. In operation, preferably a light diffusing means will be inserted in body section 10 to ensure that the LEDs on light module 20 appear to emit a single uniform frequency of light.

Figure 8:
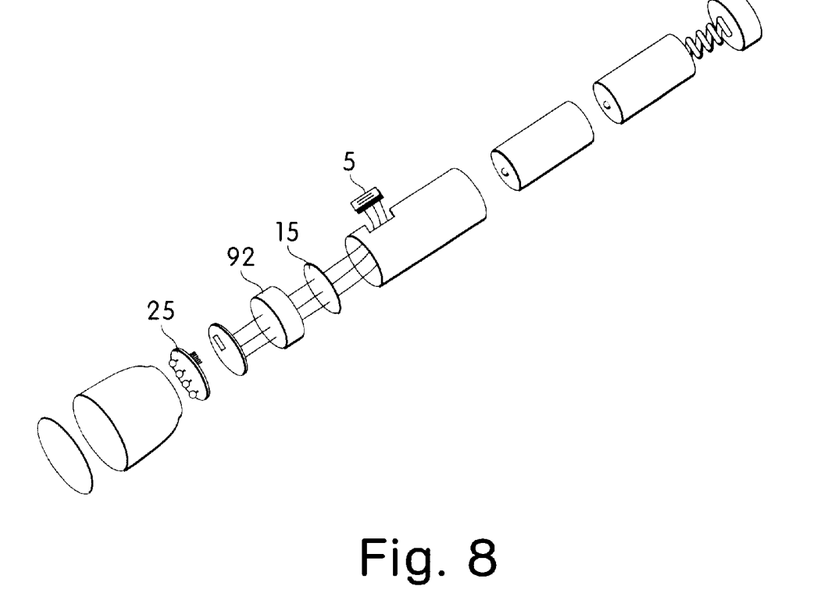
FIG. 8 is an exploded view of a flashlight assembly containing the LED lighting module of the present invention.

From the foregoing, it will be appreciated that PWM current control of LEDs to produce multiple colors may be incorporated into countless environments, with or without networks. For instance, FIG. 8 shows a hand-held flashlight can be made to shine any conceivable color using an LED assembly of the present invention. The flashlight contains an external adjustment means 5, that may be for instance a set of three potentiometers coupled to an appropriately programmed microcontroller 92 through respective A/D conversion means 15. Each potentiometer would control the current duty cycle, and thus the illumination intensity, of an individual color LED on LED board 25. With three settings each capable of generating a different byte from 0 to 255, a computer-controlled flashlight may generate twenty-four bit color. Of course, three individual potentiometers can be incorporated into a single device, such as a track ball or joystick, so as to be operable as a single adjuster. Further, it is not necessary that the adjustment means must be a potentiometer. For instance, a capacitive or resistive thumb plate may also be used to program the two or three registers necessary to set the color. A lens assembly 93 may be provided for reflecting the emitted light. A non-hand held embodiment of the present invention may be used as an underwater swimming pool light. Since the present invention can operate at relatively low voltages and low current, it is uniquely suited for safe underwater operation.

Figure 9:
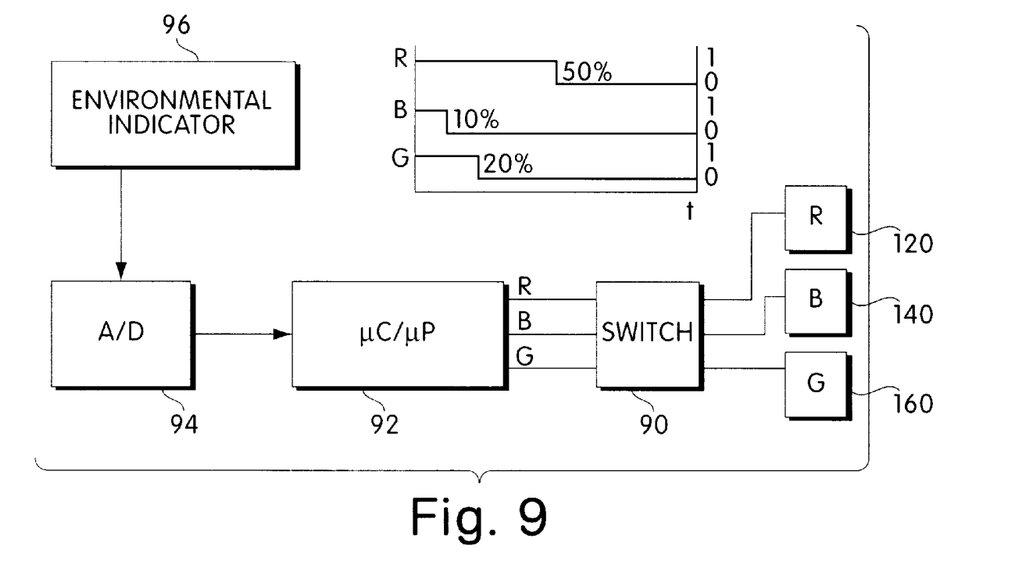
FIG. 9 is a control block diagram of the environmental indicator of the present invention.

Similarly, the present invention may be used as a general indicator of any given environmental condition. FIG. 9 shows the general functional block diagram for such an apparatus. Shown within FIG. 9 is also an exemplary chart showing the duty cycles of the three color LEDs during an exemplary period. As one example of an environmental indicator 96, the power module can be coupled to an inclinometer. The inclinometer measures general angular orientation with respect to the earth's center of gravity. The inclinometer's angle signal can be converted through an A/D converter 94 and coupled to the data inputs of the microcontroller 92 in the power module. The microcontroller 92 can then be programmed to assign each discrete angular orientation a different color through the use of a lookup table associating angles with LED color register values. The microcontroller 92 may be coupled to a transceiver 95 for transmitting and receiving signals. A current switch 90, coupled to the microcontroller 92, may be used to control the current supply to LEDs 120, 140, and 160 of different colors. The "color inclinometer" may be used for safety, such as in airplane cockpits, or for novelty, such as to illuminate the sails on a sailboat that sways in the water. Another indicator use is to provide an easily readable visual temperature indication. For example, a digital thermometer can be connected to provide the microcontroller a temperature reading. Each temperature will be associated with a particular set of register values, and hence a particular color output. A plurality of such "color thermometers" can be located over a large space, such as a storage freezer, to allow simple visual inspection of temperature over three dimensions.

Another use of the present invention is as a lightbulb. Using appropriate rectifier and voltage transformation means. the entire power and light modules may be placed in an Edison-mount (screw-type) lightbulb housing. Each bulb can be programmed with particular register values to deliver a particular color bulb, including white. The current regulator can be pre-programmed to give a desired current rating and thus preset light intensity. Naturally, the lightbulb will have a transparent or translucent section that allows the passage of light into the ambient While the foregoing has been a detailed description of the preferred embodiment of the invention, the claims which follow define more freely the scope of invention to which applicant is entitled. Modifications or improvements which may not come within the explicit language of the claims described in the preferred embodiments should be treated as within the scope of invention insofar as they are equivalent or otherwise consistent with the contribution over the prior art and such contribution is not to be limited to specific embodiments disclosed.

We claim:

1. Light apparatus comprising:
   a power terminal;
   at least one LED coupled to the power terminal;
   a current sink coupled to the at least one LED, the current sink comprising an input responsive to an activation signal that enables flow of current through the current sink;
   an addressable controller having an alterable address, the controller coupled to the input and having timing means for generating the activation signal for a predefined portion of a timing cycle;
   the addressable controller further comprising means for receiving data corresponding to the alterable address and indicative of the predefined portion of the timing cycle.

2. The light apparatus of claim 1 wherein the predefined portion represents the duty cycle of a PWM signal and the timing cycle is the PWM period.

3. A modular LED illumination assembly comprising
   a power module having a terminal for attachment to a power supply; and
   a light module comprising a plurality of LEDs and having an electrical connector removably attachable to the power module,
   the power module further comprising a current regulator for controlling maximum current supplied to the plurality of LED's, and the light module further comprising means for programming the current regulator, whereby the light module is capable of being conveniently interchanged with a different light module having a different light intensity rating.

4. An illumination apparatus comprising:
   a plurality of LEDs of at least two different colors adapted to be coupled to a power source and to a common potential reference;
   a current sink interposed between the plurality of LEDs and the common potential reference, the current sink comprising at least two switches corresponding to respective current paths of the at least two different color LEDs;
   control means for periodically and independently opening and closing the at least two switches at high frequency and for generating a duty cycle thereby;
   programming means coupled to the control means for programming respective duty cycles for each color of the at least two different color LEDs.

5. The apparatus of claim 4 wherein the duty cycle ranges from a minimum to a maximum, and the programming means is adapted to generate a substantially continuous range of duty cycles between the minimum and the maximum.

6. The apparatus of claim 4 wherein the programming means comprises respective potentiometers for each color of the at least two different color LEDs each having an independently adjustable setting, and the control means comprises an analog-to-digital converter for converting each independently adjustable setting into a numerical value indicative of each respective duty cycle.

7. The apparatus of claim 4 comprising a housing that substantially encloses the plurality of LEDs, the current sink, the control means and the programming means.

8. The apparatus of claim 7 wherein the housing is hand-held.

9. An Edison-mount lightbulb comprising:
   voltage regulating means for converting an AC potential into a DC power source;
   a plurality of LEDs of at least two different colors adapted to be coupled to the DC power source and to a common potential reference;
   a light-transmitting enclosure surrounding the plurality of LEDs;
   a current sink interposed between the plurality of LEDs and the common potential reference, the current sink comprising at least two switches corresponding to respective current paths of the at least two different color LEDs;
   control means for periodically and independently opening and closing the at least two switches at high frequency and for generating a duty cycle thereby.

10. The lightbulb of claim 9 wherein the duty cycle is predefined and uniform, whereby the lightbulb permanently generates a single unalterable color of light.

11. A method for controlling current through an LED assembly comprising the steps of:
   providing a memory location;
   placing a numerical value in the memory location indicative of the duty cycle of a pulse width modulated waveform;
   closing an LED circuit between supply and ground when the waveform is in one state, and opening the LED circuit when the waveform is in another state;
   changing the numerical value in the memory location upon receipt of a new numerical value over a computer network.

* * * * *